United States Patent [19]

Tucker

[11] 4,215,175

[45] Jul. 29, 1980

[54] NON-WOVEN FIBERS COATED WITH A POLYMER OF ETHYLENICALLY UNSATURATED BLOCKED AROMATIC DIISOCYANATES

[75] Inventor: Harold A Tucker, Shaker Heights, Ohio

[73] Assignee: The B. F. Goodrich Company, Akron, Ohio

[21] Appl. No.: 25,625

[22] Filed: Mar. 30, 1979

Related U.S. Application Data

[62] Division of Ser. No. 904,128, May 8, 1978, abandoned, which is a division of Ser. No. 734,916, Oct. 22, 1976, Pat. No. 4,101,491, which is a division of Ser. No. 550,627, Feb. 18, 1975, Pat. No. 4,008,247, which is a division of Ser. No. 412,325, Nov. 2, 1973, abandoned.

[51] Int. Cl.² .................. C08L 35/02; D02E 3/00
[52] U.S. Cl. .................................... 428/375; 428/288; 428/392; 428/393; 428/394; 428/537; 428/423.7; 428/425.1; 428/423.5; 428/425.6; 428/425.5

[58] Field of Search ............... 428/375, 392, 394, 393, 428/423, 424, 537, 288; 260/29.6 R, 29.6 T, 29.6 TA, 29.6 H, 29.6 ME, 29.6 MN; 526/258, 259, 261, 301

[56] References Cited

U.S. PATENT DOCUMENTS

| | | |
|---|---|---|
| 2,882,260 | 4/1959 | Bartl . |
| 3,721,645 | 3/1973 | Zemlin . |
| 3,897,381 | 7/1975 | Tugukuni et al. ............ 260/29.6 R |
| 3,914,335 | 10/1975 | Tugukuni et al. . |

*Primary Examiner*—Lorraine T. Kendell
*Attorney, Agent, or Firm*—Nestor W. Shust

[57] ABSTRACT

Ethylenically unsaturated blocked aromatic diisocyanates are prepared which readily polymerize to form homopolymers and interpolymers with copolymerizable vinylidene monomers. Polymers can be prepared via emulsion polymerization, and exhibit excellent stability to hydrolysis when stored in latex form. The polymers cure at temperatures as low as 80° C., and under acidic, neutral, or basic pH conditions. Homopolymers and interpolymers of the defined diisocyanates are useful as adhesives, and interpolymers of the ethylenically unsaturated blocked aromatic diisocyanates with acrylate monomers are particularly useful as binders for nonwoven fibers.

1 Claim, No Drawings

NON-WOVEN FIBERS COATED WITH A POLYMER OF ETHYLENICALLY UNSATURATED BLOCKED AROMATIC DIISOCYANATES

This is a division of application Ser. No. 904,128, filed May 8, 1978, now abandoned, which in turn is a division of application Ser. No. 734,916 filed Oct. 22, 1976, now U.S. Pat. No. 4,101,491, which in turn is a division of Ser. No. 550,627, filed Feb. 18, 1975, now U.S. Pat. No. 4,008,247, which in turn is a division of Ser. No. 412,325, filed Nov. 2, 1973, now abandoned.

BACKGROUND OF THE INVENTION

Prior art disclosing polymerizable blocked isocyanates is as follows: U.S. Pat. Nos. 2,483,194; 2,556,437; 2,882,260; 3,261,817; 3,299,007; 3,542,739 and 3,694,146, and British Pat. No. 1,288,225. Other relevant art is disclosed in U.S. Pat. Nos. 3,519,478; 3,694,389 and 3,711,571.

The novel ethylenically unsaturated blocked aromatic diisocyanates can be distinguished from other known polymerizable isocyanates by their ease of polymerization and copolymerization with vinylidene monomers, particularly in emulsion polymerization systems. The prepared polymers are quite stable to hydrolysis and can be stored in latex form.

Interpolymers of the novel diisocyanates with acrylate monomers have particular utility as binders for non-woven fibers such as paper, cotton, synthetic fibers, and the like. The fibers are coated or impregnated with the interpolymers which can then be cured at temperatures as low as 80° C. and under acidic, neutral, or basic pH conditions. This is in contrast to the known acrylic or nitrile latex binders which require highly acidic (pH of about 2) conditions to exhibit a strong fast cure at low temperatures. The highly acidic environment is undesirable as it can degrade some fibers, especially cellulose-type fibers, it can interfere with efforts to thicken the latex for more convenient use, and it can cause corrosion.

SUMMARY OF THE INVENTION

Ethylenically unsaturated blocked aromatic diisocyanates are prepared having the formula

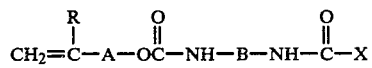

where R is hydrogen or a methyl or ethyl radical, A is a carbonyloxyalkylene radical containing 2 to about 8 carbon atoms or an aralkylene radical; B is a bivalent aromatic radical selected from the group consisting of arylene, napthalene, and the structure

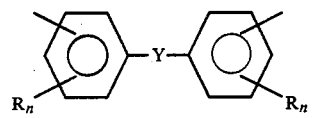

where Y is O, S or $-(CH_2)_n-$, where n=0 to 3, and X is the radical fragment remaining by the removal of a hydrogen atom from the nitrogen atom of an oxime, benzimidazole, pyrazole, benzotriazole, caprolactam or thiocaprolactam, or p-nitroaniline.

The defined diisocyanates are readily polymerized, especially via emulsion polymerization techniques, to form polymers of from about 0.1 percent to 100 percent by weight (i.e., homopolymers) of the diisocyanate and up to 99.9 percent by weight of a copolymerizable vinylidene monomer.

DETAILED DESCRIPTION OF THE INVENTION

The ethylenically unsaturated blocked aromatic diisocyanates have the formula

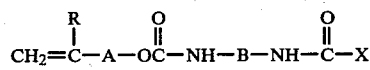

wherein R is hydrogen or a methyl or ethyl radical; A is either a carbonyoxyalkylene radical containing 2 to about 8 carbon atoms or an aralkylene radical containing 7 to about 12 carbon atoms; B is a bivalent aromatic radical selected from the group consisting of arylene, napthalene, and the structure

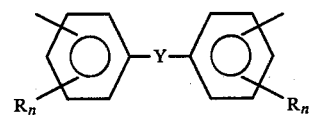

where R is defined as above, Y is O, S, or $-(CH_2)_n-$, n=0 to 3, and X is the radical fragment remaining after a hydrogen atom is removed from the nitrogen atom of an oxime, benzimidazole, pyrazole, benzotriazole, caprolactam, thiocaprolactam, or p-nitroaniline. The aromatic rings in A and/or B can be further substituted with 1 to 4 carbon atom alkyl radicals. More preferredly, R is hydrogen or a methyl radical, B is selected from the group consisting of phenylene, tolylene, naphthalene, and the defined structure where Y is $-(CH_2)_n-$ group and n=0 to 1.

Examples of the unsaturated blocked aromatic diisocyanates are:

When "A" is a carbonyloxyalkylene radical:

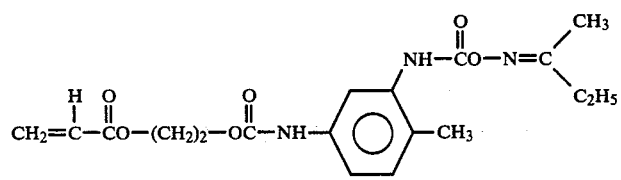

-continued
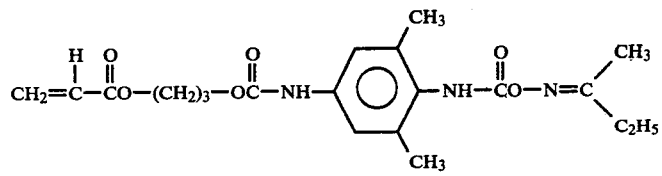
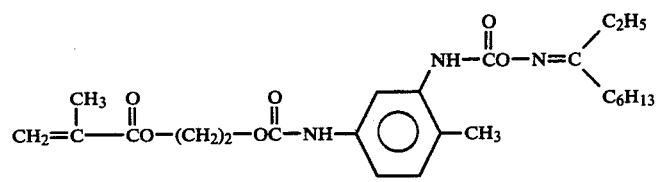
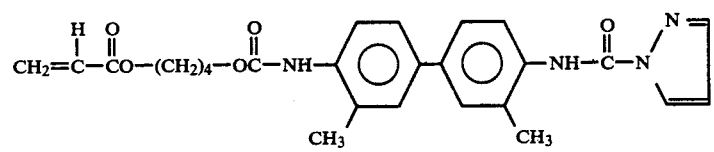
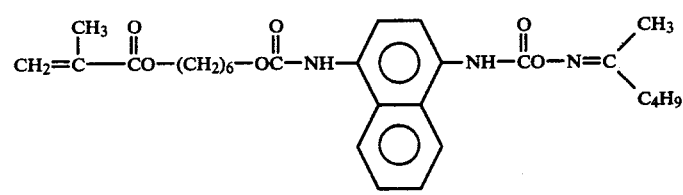
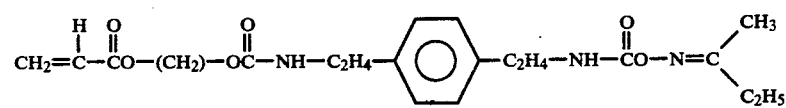
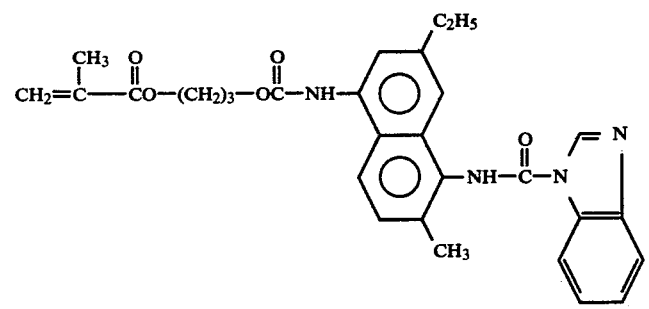
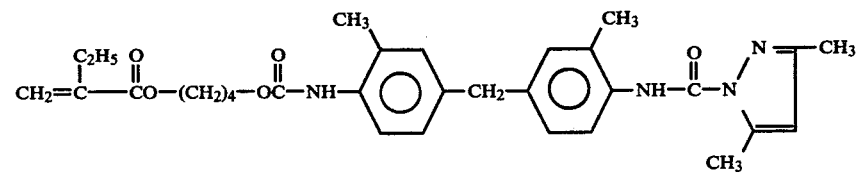
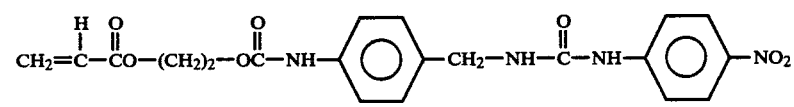
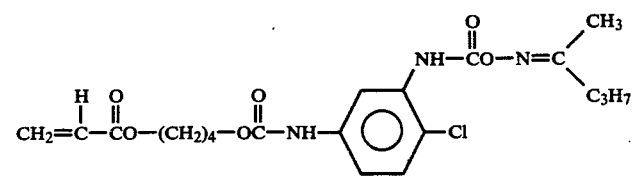

-continued
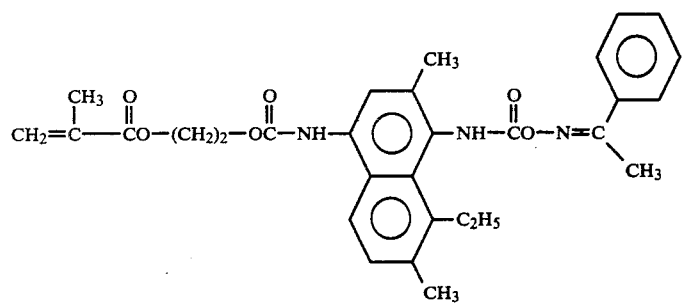
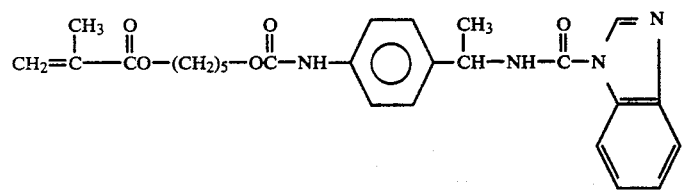
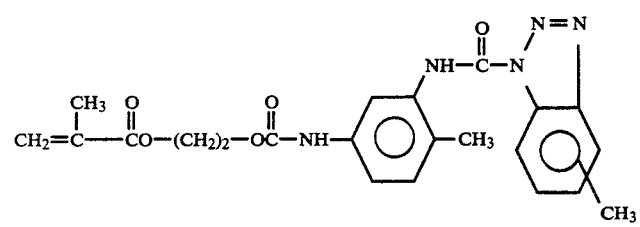
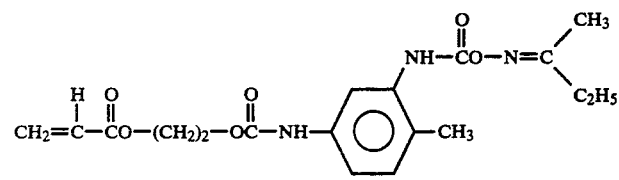
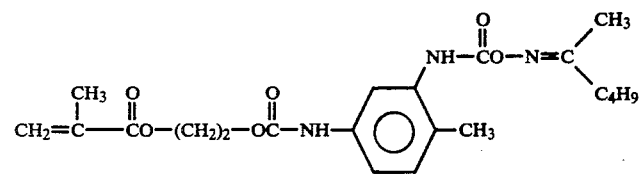
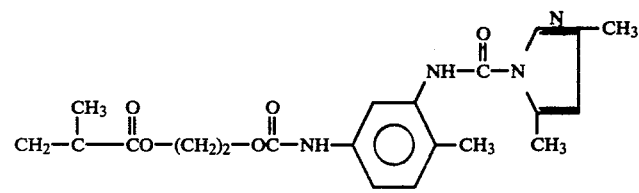
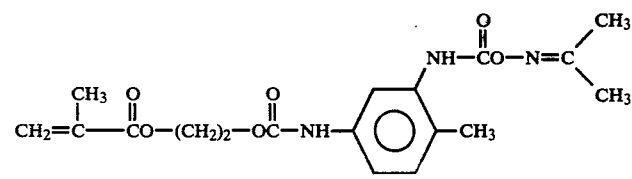
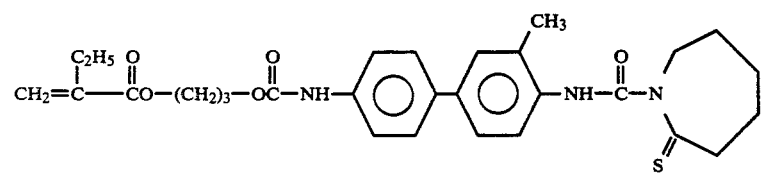

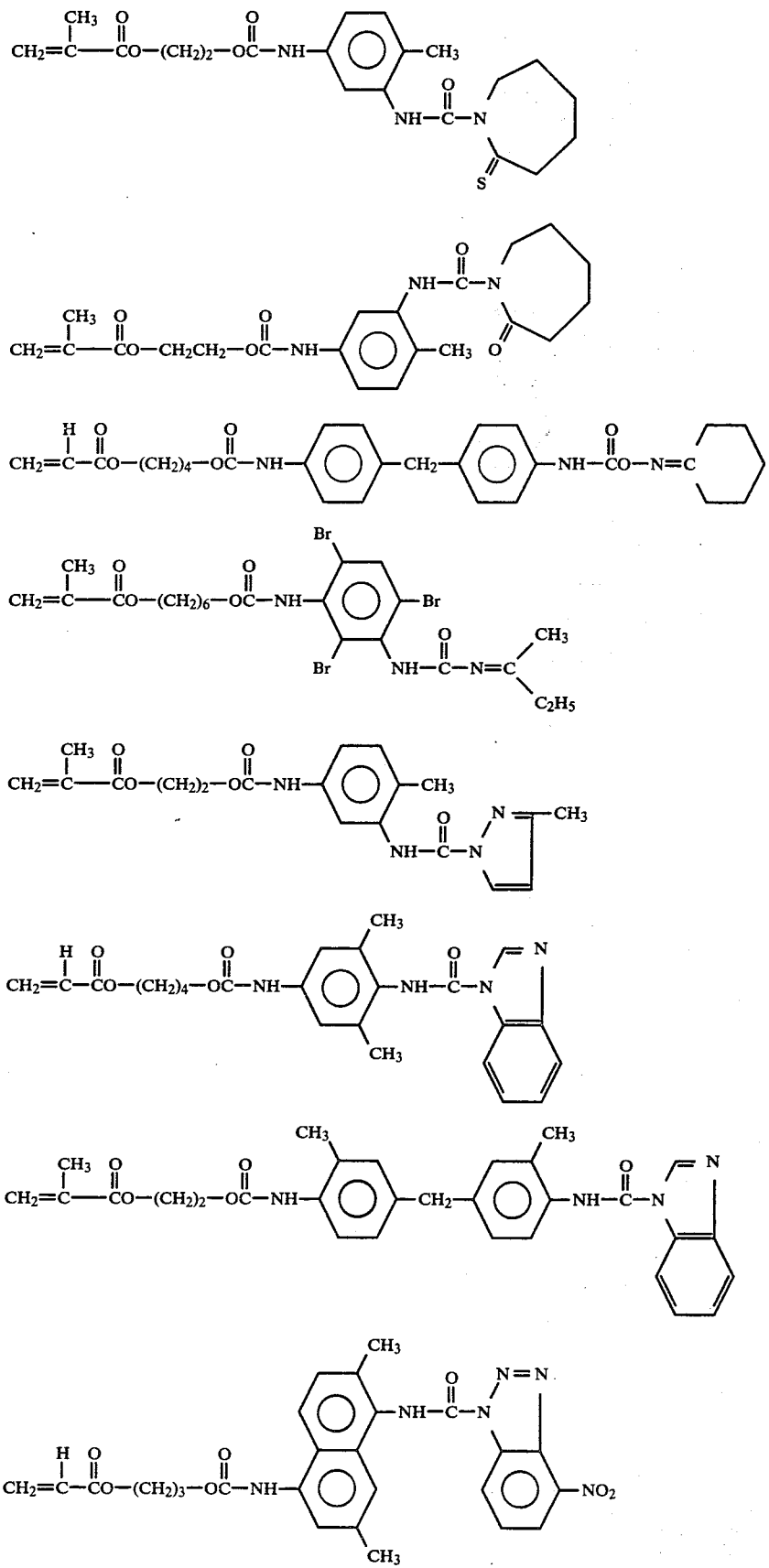

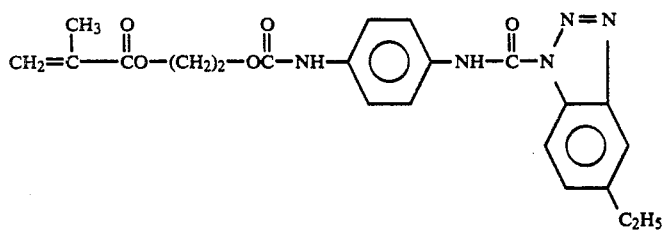
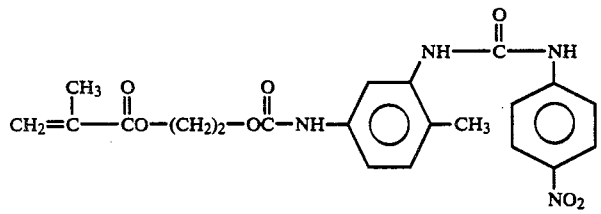
and the like.
When "A" is an arylene radical:
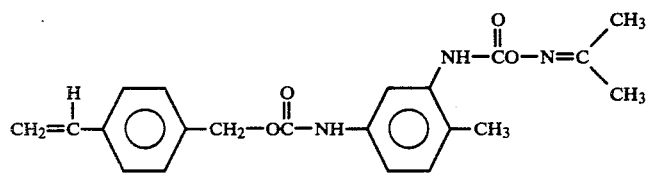
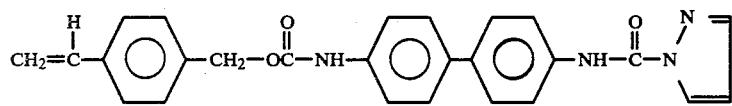
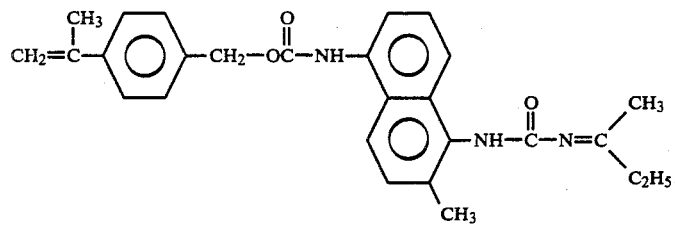
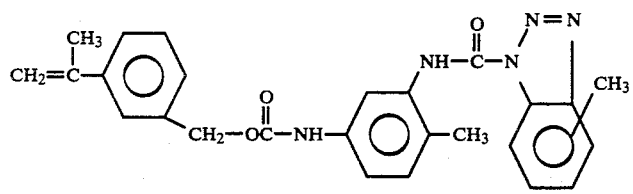
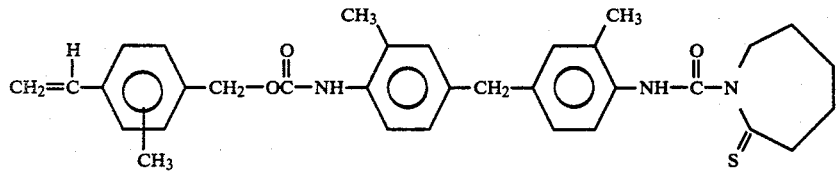
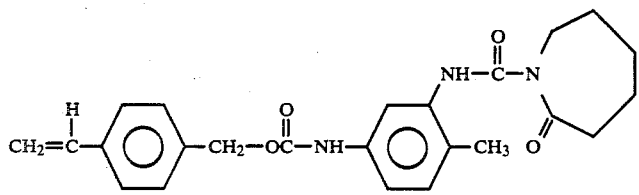

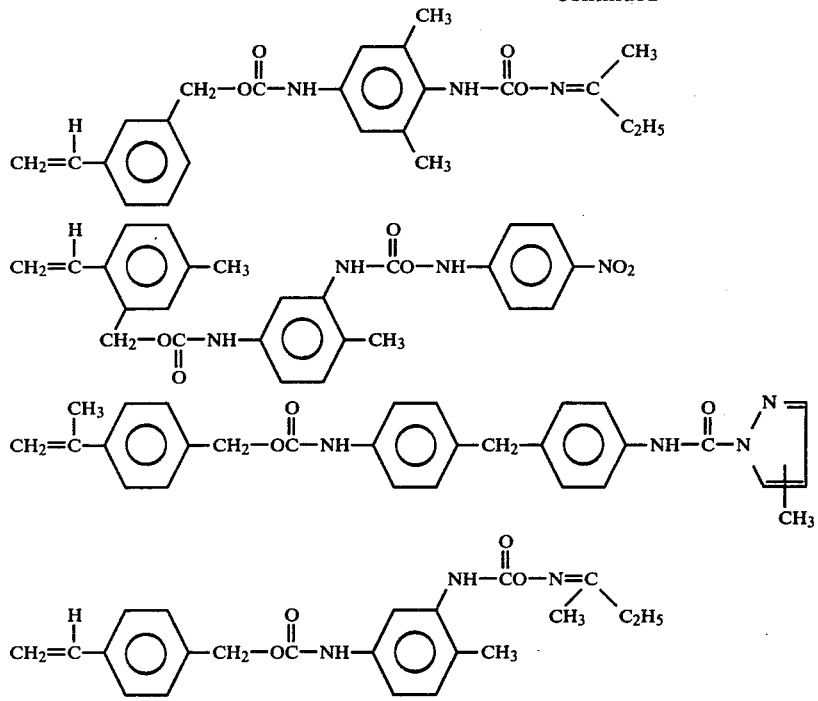

and the like.

The ethylenically unsaturated blocked aromatic diisocyanates are prepared in a two-step process wherein first a hydroxy-containing vinylidene monomer is reacted with an aromatic diisocyanate, and the product obtained then reacted with a blocking agent. Reference is made to U.S. Pat. No. 2,958,704, and the process disclosed therein.

The hydroxyl-containing vinylidene monomer has the formula

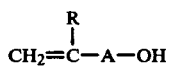

where A and R are defined as above. When A is a carbonyloxyalkylene radical, examples of the monomer include 2-hydroxyethyl acrylate, 2-hydroxyethyl methacrylate, 3-hydroxypropyl acrylate, 4-hydroxybutyl methacrylate, 4-hydroxybutyl ethacrylate, 5-hydroxypentyl acrylate, 5-hydroxy-3-methylpentyl acrylate, 6-hydroxyhexyl acrylate, and the like. When A is an aralkylene or alkyl substituted aralkylene radical, examples include o, m, and p-vinyl benzyl alcohol, o-methyl-p-vinyl benzyl alcohol, and the like.

The hydroxyl-containing monomer is reacted with an aromatic diisocyanate using at least a slight molar excess of the diisocyanate. Temperature of reaction is from about 0° C. to 100° C. The reaction must be conducted free of water. Solvents for the reaction are benzene, toluene, chlorobenzene, chloroform, carbon tetrachloride, trichloroethylene, and the like. The aromatic diisocyanates have the formula OCN—G—NCO wherein B is defined as above. Examples of these diisocyanates are 2,4-toluene diisocyanate, 2,6-toluene diisocyanate, naphthalene-1,4-diisocyanate, diphenyl diisocyanate, diphenylmethanep,p'-diisocyanate, dimethylphenylether diisocyanate, 3,3'-dimethyl-4,4'-biphenyl diisocyanate, p-isocyanatobenzyl isocyanate, bis(2-isocyanatoethyl)benzene, and the like. Halogenated diisocyanates such as 1-chloro-2,4-diisocyanatobenzene, tetrachloro-1,3-phenylene diisocyanate, 2,4,6-tribromo-1,3-phenylene diisocyanate, and the like, can be used.

The more preferred aromatic diisocyanates are those wherein one of the isocyanate groups has a 1 to 4 carbon atom alkyl group ortho to one of the isocyanate groups. Examples of these are 2,4-toluene diisocyanate, 2,6-toluene diisocyanate, and ortho-methyl substituents of other aromatic diisocyanates such as 2-methyl-1,4-naphthalene diisocyanate, 5-methyl-diphenyl diisocyanate, 2,6-dimethyltoluene-1,4-diisocyanate, 3-ethyl-1,4-toluene diisocyanate, 1,6-dimethyl-2,4-toluene diisocyanate, 3,6-dimethyl-5-ethyl-1,4-naphthalene diisocyanate, and the like.

The ortho-substituted aromatic diisocyanates are preferred, as the unhindered isocyanate group will react first and, preferentially, with the hydroxyl group of the monomer. The hindered isocyanate group tends to remain apart from this reaction and good yields of the unsaturated aromatic isocyanate are obtained. The product obtained is reacted with a compound having a labile hydrogen atom to block the remaining isocyanate group.

The choice of a compound to be used as a blocking agent is particularly crucial to the successful use of a blocked isocyanate in nonwoven fiber bonding applications. If the blocking agent-isocyanate reaction product is too stable, the agent will not release quickly and/or at moderate temperatures. High temperatures and long heating times can degrade the polymers and the nonwoven fibers. Many tertiary alcohols, phenols, amines, and imines were found to be unsatisfactory for this reason. If the blocking agent-isocyanate reaction product is too labile, the agent will release prematurely and the isocyanate will be free to react. This results in instability of the interpolymer latex or solution and problems in applying and heat curing. The novel interpolymers of this invention provide an improved balance between polymer stability and quick, moderate temperature cure cycles. This balance is struck and the excellent properties obtained only when a combination of an aromatic diisocyanate and the specified blocking agents are employed.

Blocking agents for the ethylenically unsaturated aromatic diisocyanates are oximes, benzimidazole, pyrazoles, benzotriazoles, caprolactam, thiocaprolactam, and p-nitroaniline.

The oximes are aldoximes or ketoximes of the formula

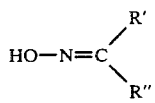

wherein R' is an alkyl radical containing 1 to about 8 carbon atoms, a cycloalkyl radical containing 4 to 8 carbon atoms, an aryl radical containing 6 to about 12 carbon atoms, or where R' and R", together with the carbon atom, form a carbon ring of 4 to 8 carbon atoms, and R" is hydrogen or the same as R'. Examples of the oximes are acetoxime, methylethyl ketoxime, methylpropyl ketoxime, methylisobutyl ketoxime, ethylhexyl ketoxime, cyclohexanone oxime, benzophenone oxime, benzoaldoxime, and the like.

Pyrazole and 1 to 4 carbon atom alkyl substituents thereof can be employed. Examples are pyrazole, 3-methyl pyrazole, 3,5-dimethyl pyrazole, and the like.

The benzotriazoles are benzotriazole and 1 to 4 carbon atom alkyl, halogen, and nitro substituents thereof. Examples of the benzotriazoles are benzotriazole, 5-methylbenzotriazole, 6-ethylbenzotriazole, 5-chlorobenzotriazole, 5-nitrobenzotriazole, and the like.

The blocking agents are employed on about a 1 to 1 mole basis of isocyanate to agent. The reaction temperature is from about 30° C. to about 110° C. Reaction time is from about 1 hour to about 15 hours. Suitable solvents for the reaction are aromatic hydrocarbon solvents such as benzene and toluene.

The ethylenically unsaturated blocked aromatic diisocyanates can be polymerized using emulsion (latex), suspension, solution, and bulk techniques known to those skilled in the art. The polymerization can be performed as a batch reaction, or one or more ingredients can be proportioned during the run. Temperature of polymerization ranges from about −10° C. to about 100° C., whereas a more preferred range is from about 5° C. to about 80° C.

The polymerization is initiated by free-radical generating agents. Examples of such agents are organic peroxides and hydroperoxides such as benzoyl peroxide, dicumyl peroxide, cumene hydroperoxide, paramethane hydroperoxide, and the like, used alone or with redox systems; diazo compounds such as azobisisobutyronitrile, and the like; persulfate salts such as sodium, potassium, and ammonium persulfate, used alone or with redox systems; and the use of ultraviolet light with photo-sensitive agents such a benzophenone, triphenylphosphine, organic diazos, and the like.

Typical emulsion polymerization ingredients would include a persulfate salt or organic peroxide and usually a redox system, water adjusted to a desired pH with acids or bases and usually buffered with inorganic salts and either anionic, cationic, or nonionic surface active agents well known to the art.

The polymerization normally is continued until about 90% or more conversion of monomers is obtained. The resulting latex can be coagulated to isolate the polymer. Typical coagulation procedures are salt/acid coagulations, use of polyvalent metal salts such as $MgSO_4$, use of alcohols such as methanol and isopropyl alcohol, and freeze agglomeration techniques. The polymer is then usually washed with water and dried.

The polymers are comprised of from 0.1 percent to 100 percent by weight (i.e., homopolymers) of an ethylenically unsaturated blocked aromatic diisocyanate(s), as defined, and up to 99.9 percent by weight, and more preferably up to about 70 percent by weight, of a copolymerizable vinylidene monomer. This monomer is a vinyl monomer having a terminal vinylidene ($CH_2=C<$) group. Examples of these monomers are acrylates and methacrylates such as ethyl acrylate, n-butyl acrylate, octyl acrylate, dodecyl acrylate, methyl methacrylate, phenyl acrylate, cyclohexyl acrylate, and the like; vinyl and allyl esters such as vinyl acetate, vinyl propionate, vinyl butyrate, allyl acetate, and the like; vinyl ketones such as methyl vinyl ketone, propyl vinyl ketone, and the like; vinyl and allyl ethers such as vinyl methylether, vinyl ethylether, vinyl isobutylether, allyl methylether, and the like; vinyl aromatics such as styrene, α-methylstyrene, p-chlorostyrene, vinyl toluene, vinyl naphthalene, and the like; vinyl nitriles such as acrylonitrile, methacrylonitrile, α-chloroacrylonitrile, and the like; dienes such as butadiene, isoprene, chloroprene, 2-isopropyl-1,3-butadiene, and the like; α-monoolefins such as ethylene, propylene, 1-butene, 1-hexene, and the like; vinyl halides such as vinyl chloride, vinyl fluoride, vinylidene chloride, and the like; and divinyls such as divinyl benzene, divinyl ether, diethylene glycol diacrylate, and the like. In addition, because the isocyanate is blocked, so-called reactive monomers can be copolymerized with the acrylates and unsaturated isocyanate. Examples of these monomers are vinyl carboxylic acids such as acrylic acid, methacrylic acid, ethacrylic acid, 2-hexanoic acid, and the like; vinyl amides such as acrylamide, methacrylamide, N-methyl methacrylamide, diacetone acrylamide, and the like; hydroxyl-containing vinyl monomers such as allyl alcohol, vinyl benzyl alcohol, β-hydroxyethyl acrylate, α-hydroxypropyl acrylate, 4-hydroxybutyl acrylate, β-hydroxyethyl methacrylate; N-methylol acrylamide, and the like.

The polymers are high molecular weight solids having dilute solution viscosities (DSV) of over 0.5 measured on a 0.2 gram sample of the polymer in 100 milliliters of solvent at 25°0 C. The polymers are cured at temperatures as low as 80° C. and can be cured under acidic, neutral, or basic pH conditions.

The polymers can be admixed with cure ingredients and compounding ingredients using two-roll mills, internal mixers such as Banburys and extruders, and like equipment.

The polymers, as isolated solid rubbers, can be cured to prepare useful vulcanizates. Compounding ingredients well known to the art can be used, such as fillers, oils and plasticizers, antioxidants, and the like. Standard mixing and cure techniques are employed. Upon heating the polymer, the blocking agent is released. Hydroxyl, carboxyl, and amine containing materials are used as curing agents. For example, glycols, polyols, polyalkylene amines, hydroxyl and carboxyl containing polyesters and polyethers, hydroxyl, carboxyl, and amine terminated vinylidene polymers, etc., and water itself, are all known and suggested reactants for isocyanate-containing materials. If the interpolymer itself contains hydroxyl, carboxyl, or amine groups, the polymer can be considered self-curing. Upon heating, the isocyanate is released and the polymer can undergo intra- and inter-molecular crosslinking.

The polymers do not have to be isolated, but can be readily stored in latex or solution form. The novel polymers have excellent stability in latex form. In non-woven binder applications, the polymers are conveniently used as latexes or solutions to coat or impregnate the fibers. Fillers, extenders, and other ingredients such as stabilizing agents, thickeners, antioxidants, and the like, are readily admixed with the latexes or solutions prior to use.

In non-woven fiber binder applications, the ethylenically unsaturated blocked aromatic diisocyanates are preferably copolymerized with an acrylate monomer. The interpolymer comprises from about 0.5 percent to about 50 percent by weight of the diisocyanate(s) as defined, and from about 50 percent to about 99.5 percent by weight of an acrylate monomer(s). More preferably, the interpolymer contains from about 1 percent to about 30 percent by weight of the diisocyanate, from about 70 percent to about 99 percent by weight of an acrylate monomer, and up to 20 percent by weight of another copolymerizable vinylidene monomer, all present as interpolymerized units.

The acrylate monomer has the formula

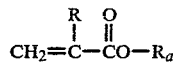

wherein R is H, —CH$_3$ or —C$_2$H$_5$, and R$_a$ is an alkyl radical containing 1 to about 24 carbon atoms, an alkoxyalkyl or alkylthioalkyl radical containing a total of 2 to about 12 carbon atoms, or a cyanoalkyl radical containing 2 to about 12 carbon atoms total. The alkyl structure can be linear or branched. Examples of the acrylates are methyl acrylate, ethyl acrylate, n-propyl acrylate, isopropyl acrylate, isobutyl acrylate, n-pentyl acrylate, isoamyl acrylate, n-hexyl acrylate, 2-methylpentyl acrylate, n-octyl acrylate, 2-ethylhexyl acrylate, n-decyl acrylate, n-dodecyl acrylate, n-tetradecyl acrylate, n-octadecyl acrylate, n-eicosyl acrylate, and the like; methyl methacrylate, ethyl methacrylate, n-hexyl methacrylate, n-octyl methacrylate, n-dodecyl methacrylate, n-octadecyl methacrylate, ethyl ethacrylate, n-butyl ethacrylate, and the like; methoxymethyl acrylate, methyl acrylate, methoxyethyl acrylate, ethoxyethyl acrylate, butoxyethyl acrylate, ethoxypropyl acrylate, methoxyethyl methacrylate, methylthioethylacrylate, hexylthioethyl acrylate, and the like; and α and β-cyanoethyl acrylate, α,β, and γ-cyanopropyl acrylate, cyanobutyl acrylate, cyanohexyl acrylate, cyanooctyl acrylate, cyanoethyl methacrylate, and the like. Often mixtures of two or more monomers and/or types of acrylate monomers are employed.

More preferably, the interpolymer contains from 70 percent to about 99 percent by weight of an acrylate monomer(s) wherein R$_a$ is an alkyl radical containing 1 to about 18 carbon atoms or an alkoxyalkyl radical containing 2 to about 8 carbon atoms. Examples of the more preferred monomers are methyl acrylate, ethyl acrylate, n-propyl acrylate, isopropyl acrylate, n-pentyl acrylate, isoamyl acrylate, n-hexyl acrylate, n-octyl acrylate, 2-ethylhexyl acrylate, n-decyl acrylate, n-dodecyl acrylate, n-octadecyl acrylate, methoxyethyl acrylate, ethoxyethyl acrylate, methoxypropyl acrylate, ethoxypropyl acrylate, and the like. Both an alkyl acrylate and an alkoxyalkyl acrylate can be used. Especially good results are obtained when employing ethyl acrylate, octyl acrylate, 2-ethylhexyl acrylate, and/or methoxyethyl acrylate.

The interpolymers are applied to the non-woven fibers using dip coating, knife edge coating, roller coating, soaking, spray coating, and like known techniques. Cure conditions depend in part upon the specific blocking agent and aromatic diisocyanate used to prepare the monomer. However, temperatures from about 80° C. to about 150° C. and more preferably from about 100° C. to about 125° C. are usually employed. Cure times range from about 3 minutes to about 30 minutes. An excellent cure is readily obtained at 100° C. in about 3 minutes at an acidic, neutral or basic pH.

Examples of non-woven fibers are papers such as Kraft paper, crepe paper, and the like, rag fibers, cotton, wool, regenerated cellulose, glass fiber, asbestos, and synthetic fibers such as polyesters, and the like. In addition to binding fibers to impart tensile strength, edge tear strength, and the like, the interpolymers are also useful as pigment and filler binders and as fabric adhesives.

The polymers can be copolymers of the essential blocked diisocyanate with acrylate monomers and from about 0.5 percent to about 10 percent by weight of a hydroxyl, carboxyl, amine or amide containing monomer. After applying such an interpolymer to a non-woven substrate and heating it, the blocking agent is released and the free isocyanate crosslinks through these reactive groups to cure the polymer. However, if the polymer does not have these groups present thereon, compounds containing the groups can be readily added to the latex or solution prior to use. These compounds are crosslinking agents, and include aliphatic and phenolic diols and polyols, diamines and polyamines, di- and polymercaptans, di- and polycarboxylic acids, and polymeric materials such as polyether polyols, polyester polyols, polyester amides, polyether amides, and the like. Examples of crosslinking agents are alkylenediols such as 1,4-butanediol, 1,6-hexanediol, 4-methyl-1,4-pentanediol, 1,10-decandiol, and the like; alicyclic diols such as 1,4-cyclohexanediol, 2-hydroxymethylcyclohexanol, and the like; phenolic diols such as p-hydroxybenzyl alcohol, hydroquinone, 2,2'-dihydroxydiphenyl, methylenebisphenol, p,p'-isopropylidene bisphenol, and the like; polyols such as 1,3,5-pentanetriol, 1,3,5-trishydroxybenzene, glycerol, sorbital, and the like; alkylenediamines such as ethylenediamine, 1,2-butylenediamine, 2-methyl-1,4-diaminobutane, hexamethylenediamine, decamethylenediamine, dodecamethylenediamine, and the like; alicyclic diamines such as 1,4-diaminocyclohexane, 1,4-diaminoethylcyclohexane, and the like; aromatic diamines such as m-phenylenediamine, m-xylylenediamine, 3,3'-diaminobiphenyl, 4,4'-diaminodiphenylmethane, p,p'-bisaminomethyl diphenylmethane, and the like; heterocyclic diamines such as piperazine, aminoethylpiperazine, and the like; polyamines such as diethylenetriamine, triethylenetetraamine, and the like; and alkanolamines such as tris(hydroxyethyl)amine, bis(hydroxyethyl)methylamine, tris(hydroxypropyl)amine, 1-amino-2-hydroxypropane, 1-aminomethylcyclohexanol, m-aminophenol, 2-amino-6-hydroxypyridine, and the like. The more preferred crosslinking agents are the alkylenediols, the alkylenediamines, and the alkanolamines.

The crosslinking agent can be added directly to the latex (or solution). It can be dissolved in a solvent such as chloroform or trichloroethylene, or suspended in water using an emulsifying agent, and then added to the latex or solution. No reaction takes place until the blocking agent is released in the cure process. The crosslinking agents are used on about a mole to mole basis of isocyanate to hydroxy, amino, etc., group. Higher levels may be used, but it is not necessary for obtaining fast strong cures.

Of course, water alone can act as a crosslinking agent for the polymers. In the presence of water, the blocked diisocyanate can react to form an amine structure which can then further react with another blocked diisocyanate group to crosslink the polymer. The water can be added to the polymer, or it can be present as residual water in the polymer or saturated non-woven. Atmospheric moisture can also act to crosslink the polymers.

As the novel interpolymers have particular utility as binders for nonwoven fibers, testing was directed to evaluation of the interpolymers in latex form as paper saturants. Actual testing included original and wet tensile strength, using an Instron tensile tester at a pull rate of 12 inches per minute. Wet tensile followed TAPPI procedure T465-m44 (specimens soaked in water for 16 hours before testing).

The following examples serve to more fully illustrate the invention.

EXAMPLE I

A series of ethylenically unsaturated blocked aromatic diisocyanates was prepared. The general reaction scheme is to first react a mole of a hydroxyl-containing vinylidene monomer with about two moles of an aromatic diisocyanate, and secondly, react the intermediate product with about 1.1 mole of a defined blocking agent per mole of the intermediate.

A. Preparation of 4-(O-methacryloyloxyethyl)urethanotolyl(2-carbamoyl)-1-tolyltriazole. The synthesis consists of a two-step reaction. Toluene, 1080 grams and 2,4-toluene diisocyanate, 1160 grams (6.66 moles), were put into a reactor vessel equipped for stirring and temperature control. The vessel was then flushed with nitrogen gas and the intermediate product reaction conducted under nitrogen gas. The mix was heated to 60° C. while stirring, and 433 grams (3.33 moles) of β-hydroxyethylmethacrylate slowly added over 5.5 hours. Temperature of the mixture rose to 65° C. and was controlled there throughout the addition. The mixture was then stirred for one hour. Total reaction time was about 7 hours.

The reactor mixture (a solution) was cooled to 5° C. and allowed to stand for about 16 hours. White crystals formed in the solution. The mixture was then cooled to −30° C. and the crystals filtered out and washed with hexane. The intermediate product was dried to yield 754 grams of a white crystalline solid having a melting point of 71°-72° C. Analyzed for isocyanate content and for unsaturation, the intermediate product proved to be about 99% pure. The yield was 74% by weight based on the theoretical weight as measured on the hydroxy compound.

The intermediate product (i.e., the β-hydroxyethylmethacrylate/2,4-toluenediisocyanate reaction product), 22.3 grams (0.0735 mole) was dissolved in 350 milliliters of toluene at about 30° C. and the solution placed into a reactor vessel. Tolyltriazole, 10.75 grams (0.0808 mole) was dissolved in 50 milliliters of toluene at about 30° C. and the solution then added to the reactor vessel. The mixture was stirred for 3 hours at 30° C. and then at 50° C. for 0.5 hour. A white precipitate forms during the stirring time. Total reaction time is about 4 hours.

The reaction mixture was cooled to 0° C. and the white precipitate isolated by filtration. The product was washed with acetonitrile and dried at 25° C. under a vacuum to yield 25.6 grams of a crystalline solid having a melting point of 132°-133.5° C. The yield was 80% based on the amount of intermediate product used. Analysis by unsaturation showed the product to be about 99% pure. The product has the structure

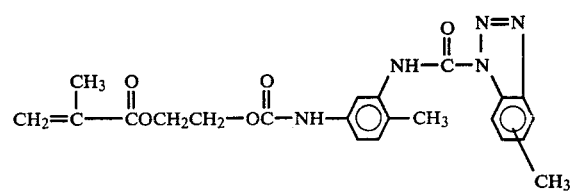

B. Preparation of 4-(O-methacryloyloxyethyl)urethanotolyl(2-carbamoyl)-2-butanone oxime. The intermediate product prepared above was employed.

Toluene, 2686 milliliters, and 517 grams (1.7 moles) of the intermediate product were placed in a reactor vessel and stirred. Methylethyl ketoxime, 152 grams (1.74 moles) was dissolved in 260 milliliters of toluene and the solution added to the reactor vessel slowly over a 1.5 hour period. Temperature of the reaction was kept at 28°-29° C. The mixture was then stirred for 16 hours at about 25° C., followed by cooling to −30° C. A white precipitate formed which was filtered out and dried to yield 494 grams of product (a 74% yield). The crystalline product has a melting point of 80.5°-82° C., and analyzed by unsaturation to be about 98% pure. The theoretical nitrogen content of the product is 10.7% by weight and the analyzed nitrogen content was measured to be 10.6% by weight. The product has the structure

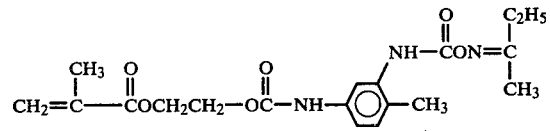

C. Following the procedure given in B above, the following compound was prepared by reacting the intermediate product with acetoxime:

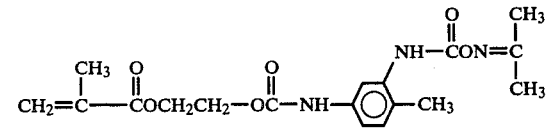

D to E. Following the procedure given in B, the intermediate product was reacted with methylisobutyloxime and dimethylpyrazole, respectively, to yield:

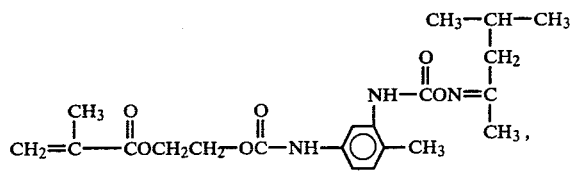

melting point of 75°–79.5° C., and

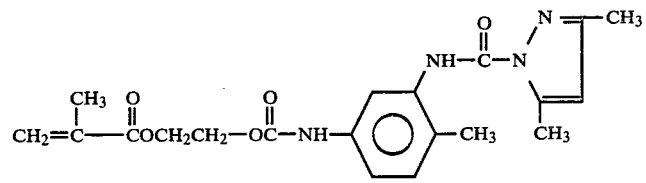

melting point of 109°–110.5° C.

F. Following the procedure given in A above, β-hydroxyethyl acrylate and 2,4-toluene diisocyanate were reacted together to form an intermediate product which was then reacted with methylethyl ketoxime. The product is

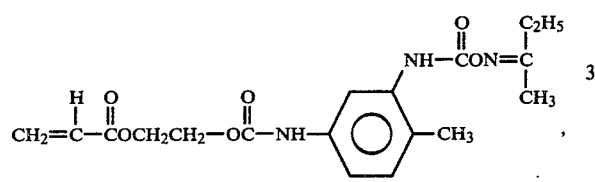

melting point of 108°–113° C. The compound was tested to be 95% pure using a standard isocyanate analysis test.

G. Following the procedure given in A above, p-vinylbenzyl alcohol was reacted with 2,4-toluene diisocyanate, followed by reaction with methylethyl ketoxime. The product is

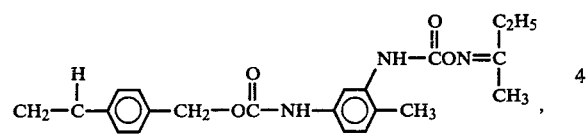

melting point of 79.5°–83° C.

EXAMPLE II

The ethylenically unsaturated blocked aromatic diisocyanate prepared in Example I in procedure B was interpolymerized with a vinylidene terminated monomer, using an emulsion polymerization system. The recipe is as follows:

| | |
|---|---|
| Ethyl acrylate, grams | 94.1 |
| Diisocyanate B[a], grams | 5.9 |
| Water, milliliters | 175 |
| Sodium lauryl sulfonate milliliters[b] | 30 |
| Naphthalene sulfonate, milliliters[b] | 9 |
| Sodium hydrosulfite, milliliters[c] | 8.3 |
| Sodium formaldehyde sulfoxalate, milliliters[d] | 10 |
| Sodium salt of ethylene diamine tetraacetic acid and sodium gluconate, milliliters[e] | 8.3 |
| p-methane hydroperoxide, milliliters | 0.2 |

[a] $CH_2=C(CH_3)—COCH_2CH_2—OC—NH—C_6H_4(CH_3)—NH—CON=C(C_2H_5)(CH_3)$
[b] 10% by weight in water
[c] 0.5% by weight in water
[d] 1.0% by weight in water
[e] 0.24 and 0.13 grams in 100 milliliters of water
[f] 50% by weight The diisocyanate was dissolved in the ethyl acrylate, and the solution admixed with the water, sodium lauryl sulfonate, sodium hydrosulfite, and naphthalene sulfonate. 17 milliliters of the mixture was placed in a reactor vessel followed by the sodium formaldehyde sulfoxalate, sodium salt of ethylene diamine tetraacetic acid and sodium glyconate, and p-menthane hydroperoxide. An immediate exotherm occurred and temperature of the reaction was controlled at 27°±3° C. Using a stirred dropping funnel, the remaining mixture was slowly added to the reactor vessel over a 1 hour period. After the addition was complete, the reactor mix stood for 16 hours. Total conversion of monomers to polymer was 96%, based on the total solids of the mix.

EXAMPLE III

Interpolymers of ethylenically unsaturated blocked aromatic diisocyanates (as prepared in Example I) and ethyl acrylate, were prepared following the procedure of Example II. The following polymeric samples were prepared and evaluated in their latex form.

| Polymer Sample | Wt. Percent Ethyl Acrylate | Diisocyanate[a] |
|---|---|---|
| A | 94 | 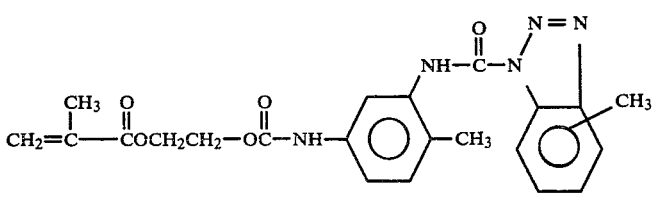 |

-continued

| Polymer Sample | Wt. Percent Ethyl Acrylate | Diisocyanate[a] |
|---|---|---|
| B | 95 | 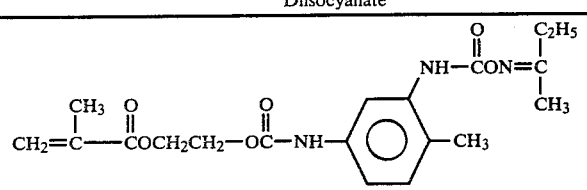 |
| C | 94 | 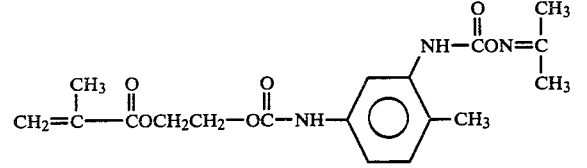 |
| D | 94 | 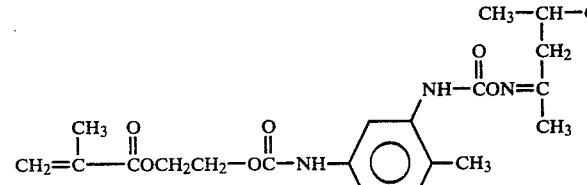 |
| E | 95 | 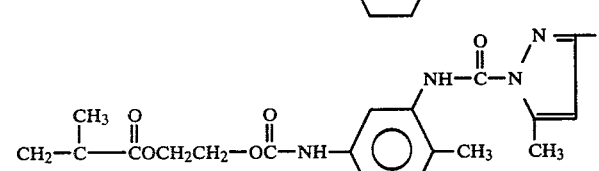 |
| F | 94 | 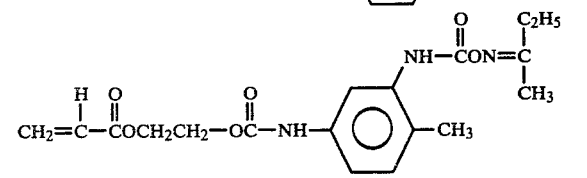 |
| G | 94 | 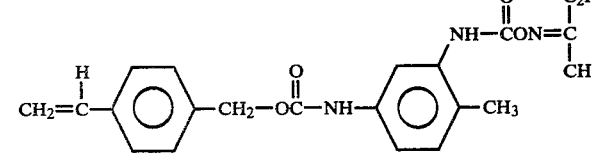 |

[a]Weight percent of diisocyanate = 100% - weight percent of ethyl acrylate

The latex samples were used at a total solids content of about 20% by weight. The non-woven fiber employed was saturation grade, bleached Kraft paper of 11 mils thickness. 8 inch by 1 inch strips of the paper were soaked in each sample latex. Solids pickup was about 50% by weight for each test strip. The strips were then dried at room temperature followed by curing at selected temperatures and times. When an added crosslinker was employed, it was dissolved in or added to the latex as a solution or suspension prior to soaking the paper strips.

Evaluation consisted of wet tensile strength testing following Tappi procedure T465-m 44. The impregnated paper strips were soaked overnight in water and then pulled on an Instron tensile tester at a jaw speed of 12 inches per minute. Test strip samples were run in triplicate and the arithmetic average reported.

The crosslinker employed in this series of experiments is either residual water (i.e., no crosslinking agent was added) or triethanol amine. When triethanol amine was used, it was simply dissolved in the latex, prior to soaking the samples, at none, one, or two mole equivalents of crosslinker per mole equivalent of isocyanate group on the polymer.

The data obtained is listed in the following table.

| Latex Sample | Parts by Wt. of Triethanol amine[a] | Wet Tensile Strength 3 Minute Cure At | | |
|---|---|---|---|---|
| | | 100° C. | 125° C. | 150° C. |
| A | none | 18 | 20 | 20 |
|  | 0.75 | 21 | 20 | 21 |
|  | 1.50 | 22 | 20 | 22 |
| B | none | 20 | 22 | 23 |
|  | 1.50 | 22 | 24 | 25 |
| C | none | 15 | 21 | 27 |
|  | 0.75 | 18 | 23 | 29 |
| D | none | 20 | 22 | 21 |
|  | 0.75 | 20 | 21 | 21 |
| E | none | 22 | 23 | 24 |
|  | 1.50 | 20 | 23 | 22 |
| F | none | 21 | 22 | 23 |
|  | 0.75 | 21 | 24 | 24 |
| G | none | 19 | 23 | 22 |

| Latex Sample | Parts by Wt. of Triethanol amine[a] | Wet Tensile Strength 3 Minute Cure At | | |
|---|---|---|---|---|
| | | 100° C. | 125° C. | 150° C. |
| | 0.75 | 20 | 23 | 24 |

[a]Parts by weight per 100 parts by weight of polymer in the latex

The data shows that excellent wet tensile strength is exhibited by all of the samples. The paper strip, without being impregnated by the novel polymers, has a wet tensile strength of about 0.5 psi. The Example shows the excellent results obtained using the novel polymers in latex form as non-woven fiber binders. The strength obtained is as good as or better than results obtained using commercial latexes, especially at low cure temperatures. For comparison, a commercial acrylic latex would exhibit, cured at 100° C. using no crosslinker, a wet tensile strength of about 4 psi at a basic pH to a high of about 16 psi at an acid pH.

EXAMPLE IV

Following up Example III in more detail, sample latex A was used to prepare wet tensile samples at various pH's of the latex. Using 0.90 parts by weight of 1,6-hexanediol as a crosslinker, after cure at 100° C. for 3 minutes, the wet tensile strength values were: pH of 5, 20 psi; pH of 7, 20 psi; and pH of 9, 19 psi. Repeating the test using 0.75 parts by weight of triethanol amine as the crosslinker, the values were: pH of 5, 21 psi; pH of 7, 21 psi; and pH of 9, 21 psi. In contrast, two commercial acrylic latexes were also evaluated as to their ability to impart wet tensile strength over a range of pH values with the following results: pH of 5, 11 psi and 6 psi, respectively; pH of 7, 8 psi and 6 psi, respectively; and pH of 9, 4 psi and 4 psi, respectively. The example shows that not only do the polymers of the invention impart greater wet tensile strength to non-wovens than known commercial latexes, compared at a 100° C. cure temperature, but the novel polymers are also not sensitive to pH as the commercial acrylic latexes are. At a cure temperature of 80° C., a test sample using the novel polymer prepared as sample B had a wet tensile strength of 14 psi (cured 3 minutes). The difference between the novel polymers of the invention and the commercial latexes diminishes as the temperature of cure increases and the pH of cure decreases. However, fast cures at low temperatures over a range of pH conditions is highly desirable.

EXAMPLE V

The ultimate tensile strength and wet tensile strength of a bound non-woven fiber is a function of both the polymeric binder and the crosslinking agent employed. Of the known crosslinking agents, the use of alcoholic amines is preferred with the novel polymers of this invention. Using the polymer latex prepared as sample A in Example III, and following the procedure given in Example III, various crosslinking agents were evaluated at one equivalent weight as to their ability to develop rapid and high strength cures.

| Sample | Crosslinking Agent | Parts by Weight[c] | Wet Tensile Strength | | | |
|---|---|---|---|---|---|---|
| | | | 80° | 100° | 125° | 150° |
| 1 | None[a] | — | 13 | 14 | 21 | 23 |
| 2 | 1,6-hexanediol | 0.90 | 17 | 17 | 21 | 23 |
| 3 | 1,10-decanediol[b] | 1.28 | 18 | 21 | 27 | 29 |
| 4 | triethanol amine | 0.75 | 20 | 21 | 25 | 25 |
| 5 | diethanol methylamine | 0.90 | 21 | 23 | 25 | 27 |
| 6 | dethanol ethylamine | 0.98 | 22 | 22 | 25 | 27 |
| 7 | 1,12-dodecanediamine[b] | 1.50 | — | 17 | 18 | 20 |

[a]Residual water acts as a crosslinker.
[b]Dissolved in chloroform and coated on wet tensile sample strip and dried.
[c]Parts by weight per 100 parts by weight of polymer in the latex.

EXAMPLE VI

The polymers of the present invention present a unique balance between rapid cure at low temperatures (evidencing quick, efficient release of the blocking agent) and stability, especially to hydrolysis in the presence of water. This unique balance is struck by the use of both the aromatic diisocyanate and the specified blocking agents in the preparation of the novel ethylenically unsaturated blocked aromatic isocyanates. The following data shows that the polymers of the invention have good stability to hydrolysis. Polymer latex sample B prepared in Example III is employed. Testing consisted of wet tensile strength before and after aging at room temperature.

| Sample B Test Strip | Wet Tensile Strength, psi | | Time Aged (days) |
|---|---|---|---|
| | Original | Aged | |
| Cured 3' at 100° C. | 20 | 14 | 50 |
| | | 12 | 100 |
| 3' at 125° C. | 22 | 19 | 50 |
| | | 17 | 100 |
| 3' at 150° C. | 23 | 19 | 50 |
| | | 18 | 100 |
| Aged in presence of 0.75 parts by wt. of triethanol amine | | | |
| Cured 3' at 100° C. | 22 | 19 | 50 |
| | 22 | 17 | 100 |

EXAMPLE VII

Expanding on Example VI, other polymers of this invention were prepared following the procedures given in Examples I and II, and evaluated as to their stability to hydrolysis and their ability to impart wet tensile strength to non-woven fibers. Original and aged wet tensile strength of impregnated non-woven paper was determined following the procedure in Example III. Results are reported in the following tables.

| Polymer Sample | Wt. Percent Vinylidene Monomer | Diisocyanate[a] |
|---|---|---|
| H | 94 EA[b] | $CH_2=C(CH_3)-COCH_2CH_2-OC-NH-C_6H_3(CH_3)-NH-CON=C(CH_3)(CH_2CH(CH_3)_2)$ with carbonyl groups |
| I | 96 EA[b] | $CH_2=C(CH_3)-COCH_2CH_2-OC-NH-C_6H_3(CH_3)-NH-CON=C(CH_3)(C_9H_{17})$ |
| J | 87 EA[b], 10 VCN[c] | $CH_2=C(CH_3)-COCH_2CH_2-OC-NH-C_6H_3(CH_3)-NHCON=C(CH_3)(C_2H_5)$ |
| K | 94 EA[b], 2 AA[d] | $CH_2=C(CH_3)-COCH_2CH_2-OC-NH-C_6H_3(CH_3)-NH-CON=C(CH_3)(C_2H_5)$ |
| L | 76 EA[b], 20 Sty[e] | $CH_2=C(CH_3)-COCH_2CH_2-OC-NH-C_6H_3(CH_3)-NHCON=C(C_2H_5)(CH_3)$ |
| M | 70 BD[f], 20 Sty[e] | $CH_2=C(CH_3)-COCH_2CH_2-OC-NH-C_6H_3(CH_3)-NHCON-C(CH_3)(C_2H_5)$ |

[a] Weight percent diisocyanate = 100% - weight percent of vinylidene monomer(s)
[b] Ethyl acrylate
[c] Acrylonitrile
[d] Acrylic acid
[e] Styrene
[f] Butadiene The polymers above, in latex form, were used to impregnate saturation grade, bleached Kraft paper (11 mils thick) following the procedure in Example III. The test sample strips were then evaluated for their original wet tensile strength. Following Example VI, after allowing the polymer latex samples to age, test sample strips were again prepared and the wet tensile strength measured. Results are reported below.

| Latex Sample | Wet Tensile Strength[1], psi Original | Aged | Days | Average % Decrease Per Day |
|---|---|---|---|---|
| B | 20 | 12 | 100 | 0.40 |
| H | 20 | 17 | 45 | 0.33 |
|   |    | 14 | 100 | 0.30 |
| I | 15 | 8 | 47 | 0.99 |
| J | 20 | 17 | 30 | 0.50 |
|   |    | 15 | 60 | 0.42 |
| K | 16[2] | 11 | 34 | 0.92 |
| L | 21 | 19 | 29 | 0.33 |
|   |    | 15 | 64 | 0.45 |
| M | 22[3] | 15 | 50 | 0.64 |

[1] Cured 3 minutes at 100° C., no crosslinker added
[2] At 15th day
[3] At 70th day The data shows that the polymers of the present invention, samples B and H to M, prepared using the novel ethylenically unsaturated blocked aromatic diisocyanates, impart good wet tensile strength to nonwoven fibers, and have unexpectedly good stability to hydrolysis when stored as a latex. If a crosslinker and/or higher cure temperatures are employed with the novel polymers, higher original and aged wet tensile strengths are obtained. For example, sample I, which showed the least stability, can be cured at 150° C. using 0.75 parts of triethanolamine (after 47 days of aging) to yield a wet tensile strength of 19 psi.

EXAMPLE VIII

If, instead of reacting the hydroxyl-containing monomer with the aromatic diisocyanate, the blocking agent is first reacted with the aromatic diisocyanate, different variations in the structure of the ethylenically unsaturated blocked aromatic diisocyanate can be prepared. For example, in Example I, procedure A, the following diisocyanate was prepared:

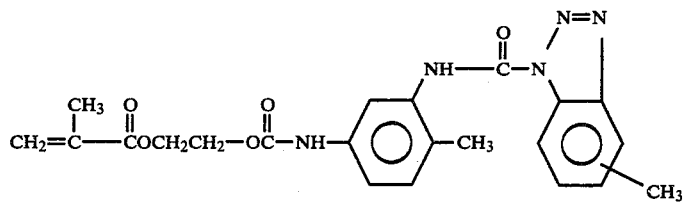

When the methylbenzotriazole was first reacted with the 2,4-toluene diisocyanate, followed by reaction with the β-hydroxyethyl acrylate, the structure is:

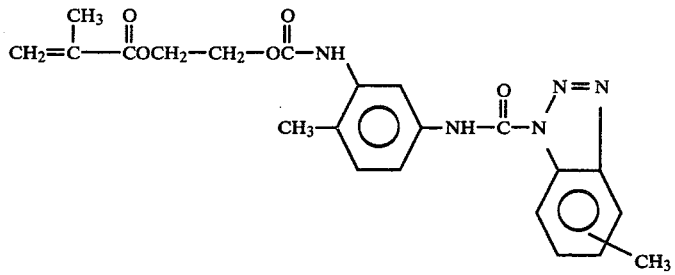

The diisocyanate prepared by the reverse addition of materials can be easily polymerized with vinylidene-terminated monomers via emulsion techniques, and is useful in latex form as a binder for non-woven fibers. The following data shows this fact.

| Latex Sample | Wet Tensile Strength, psi[b] | | | |
|---|---|---|---|---|
| | 80° C. | 100° C. | 125° C. | 150° C. |
| P[a] | 15 | 16 | 19 | 22 |

[a]96% by weight ethyl acrylate, 4% by weight diisocyanate
[b]3 minute cure

The polymer was prepared following the procedure in Example II. Testing followed the procedure in Example III. Use of an added crosslinker raises the value of the wet tensile strength.

EXAMPLE IX

Following procedures in previous Examples, the diisocyanates made in Example I as C and E were interpolymerized with ethyl acrylate and β-hydroxyethyl methacrylate. The polymers were evaluated in latex form as binders for non-woven paper. Data is as follows:

| Latex Sample | Wet Tensile Strength, psi | | |
|---|---|---|---|
| | 100° C. | 125° C. | 150° C. |
| Q[a] | 17 | 18 | 18 |
| R[b] | 15 | 21 | 24 |

[a]93.8% ethyl acrylate, 1.5% β-hydroxyethyl methacrylate, 4.7% diisocyanate E
[b]95.6% ethyl acrylate, 1.3% β-hydroxyethyl methacrylate, 3.1% diisocyanate C

EXAMPLE X

Diisocyanate sample B from Example I was interpolymerized with ethyl acrylate via an emulsion polymerization process. The recipe was:

| | |
|---|---|
| Ethyl acrylate, grams | 20.4 |
| Diisocyanate B[a], grams | 12.9 |
| Water, milliliters | 68 |
| Sodium lauryl sulfonate, milliliters[b] | 10 |
| Ammonium persulfate, grams | 6.5 |

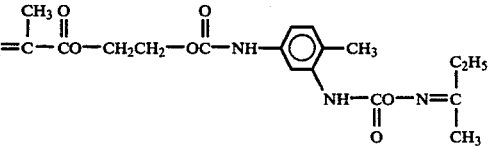

[b]10% by weight in water

The ethyl acrylate, diisocyanate B, sodium lauryl sulfate solution, and 4 milliliters of water were mixed together in a stirred dropping funnel. 2 milliliters of the mixture was then placed into the reactor vessel with 62 milliliters of water and the ammonium persulfate (dissolved in 2 milliliters of water). The temperature was raised to 50° C. and held at 55°±2° C. throughout the run. The remaining monomer mixture was added over a 20 minute period. Total reaction time was 1.5 hours. Percent conversion of monomers to polymer was 96% based on total solids. The example demonstrates that interpolymers containing high weight percents of the ethylenically unsaturated blocked aromatic diisocyanates of this invention can be readily prepared. In this example, the interpolymer composition was about 61% by weight ethyl acrylate and about 39% by weight of the specific diisocyanate.

I claim:

1. An article comprising (1) a nonwoven fiber coated or impregnated with (2) a polymer comprising from about 0.1 percent to 100 percent by weight of polymerized units of an ethylenically unsaturated blocked aromatic diisocyanate of the formula

wherein R is hydrogen or a methyl or ethyl radical; A is a carbonyloxyalkylene radical containing 2 to about 8 carbon atoms or an aralkylene radical containing 7 to about 12 carbon atoms; B is a bivalent aromatic radical selected from the group consisting of arylene, naphthalene, and the structure

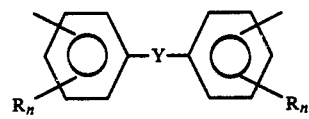

where R is defined as above; Y is O, S, or $-(CH_2)_m-$; n=0 to 3; and X is the radical fragment remaining after a hydrogen atom is removed from the nitrogen atom of an oxime, benzimidazole, pyrazole, benzotriazole, caprolactam, thiocaprolactam, or p-nitroaniline, and up to 99.9 percent by weight of polymerized units of a copolymerizable vinylidene monomer.

* * * * *